United States Patent
Lo et al.

(10) Patent No.: US 10,973,445 B2
(45) Date of Patent: Apr. 13, 2021

(54) METHOD AND DEVICE FOR OPTICAL DETECTION OF KAWASAKI DISEASE AND TREATMENT RESULT

(71) Applicant: Chien-Ming Lo, Kaohsiung (TW)

(72) Inventors: Chien-Ming Lo, Kaohsiung (TW); Yi-Dong Zhong, Xiamen (CN)

(73) Assignee: Chien-Ming Lo, Kaohsiung (TW)

( * ) Notice: Subject to any disclaimer, the term of this patent is extended or adjusted under 35 U.S.C. 154(b) by 585 days.

(21) Appl. No.: 15/866,795

(22) Filed: Jan. 10, 2018

(65) Prior Publication Data
US 2019/0209056 A1 Jul. 11, 2019

(51) Int. Cl.
*A61B 5/1455* (2006.01)
*A61B 5/00* (2006.01)
*A61B 5/145* (2006.01)
*G01N 33/68* (2006.01)

(52) U.S. Cl.
CPC .......... *A61B 5/1455* (2013.01); *A61B 5/0075* (2013.01); *A61B 5/14546* (2013.01); *A61B 5/0082* (2013.01); *G01N 33/6893* (2013.01)

(58) Field of Classification Search
CPC .............. A61B 5/1455; A61B 5/14551; A61B 5/14552; A61B 5/14536; A61B 5/0075; A61B 5/0205; A61B 5/0082
See application file for complete search history.

(56) References Cited

U.S. PATENT DOCUMENTS

| 7,280,866 B1* | 10/2007 | McIntosh ............. A61B 5/0075 600/475 |
| 2016/0310054 A1* | 10/2016 | Izzetoglu ............. A61B 5/4064 |

FOREIGN PATENT DOCUMENTS

TW  I429752 B  3/2014

* cited by examiner

*Primary Examiner* — Chu Chuan Liu
(74) *Attorney, Agent, or Firm* — Rosenberg, Klein & Lee

(57) ABSTRACT

A method and device for optical detection of Kawasaki disease and of the treatment result of Kawasaki disease are provided. At least three light waves of different wavelengths are propagated through a to-be-detected body portion of a healthy subject and a to-be-detected body portion of a person with (or suspected of) Kawasaki disease and are received after absorption, and hence attenuation, by tissues in the respective to-be-detected body portions. Attenuation of the light waves is compared against the absorption spectrum of human tissues to obtain the hemoglobin levels and water contents of the to-be-detected body portions. The hemoglobin level and water content of the person with (or suspected of) Kawasaki disease are compared with those of the healthy subject respectively so that a medical professional can evaluate the treatment result of (or diagnosis) Kawasaki disease according to the differences obtained as well as clinical experience.

13 Claims, 5 Drawing Sheets

METHOD AND DEVICE FOR OPTICAL DETECTION OF KAWASAKI DISEASE AND TREATMENT RESULT

BACKGROUND OF THE INVENTION

1. Technical Field

The present invention relates to a method and device for optical detection of Kawasaki disease and of treatment result. More particularly, the invention relates to non-invasive (i.e., optical) detection of the water content (swelling), hemoglobin level (redness), and blood oxygen level in a child's limb so that a physician can distinguish Kawasaki disease or assess the treatment result of the disease according to the detection results as well as clinical experience.

2. Description of Related Art

Kawasaki disease, which manifests mainly as systemic vasculitis, has a high incidence rate among children under the age of five and is nowadays a major cause of acquired heart disease among children in developed countries. A patient is diagnosed with Kawasaki disease if any four of the following five symptoms appear along with a fever that lasts for at least five days: conjunctivitis, "strawberry" tongue or dry cracked lips, rash all over the body, swelling or skin peeling of the limbs or extremities, and swollen lymph nodes in the neck.

Currently, most of the methods that can assist a physician in determining whether a child contracts Kawasaki disease or evaluating the treatment result of a patient diagnosed with the disease are invasive, one example of which is disclosed in Published Taiwan Patent Application No. 201028480, entitled "Detection of unhealthy cell and uses thereof".

Invasive detection, however, may frighten a child to be examined such that the child is unable or unwilling to cooperate. In addition, invasive detection more or less involves the risk of infection.

BRIEF SUMMARY OF THE INVENTION

Swelling of the extremities is typical, and one of the five major symptoms, of Kawasaki disease. According to our research results, about 90% of children with the disease exhibit this symptom, the percentage being lower only than that associated with conjunctivitis. Our research has also found that the albumin level lowers in patients with Kawasaki disease, and that the extent to which the albumin level lowers is positively correlated to the severity of the disease. Based on the foregoing findings, therefore, we developed a Kawasaki disease detection method that detects the water content (swelling), hemoglobin level (redness), and blood oxygen level of a body portion optically, providing numerical values that help increase the accuracy of diagnosis of Kawasaki disease. The optical detection method can also be used to evaluate the treatment result of the disease.

More specifically, the present invention provides a method for detecting Kawasaki disease optically through the following steps:

A. At least three light waves of different wavelengths are propagated through a to-be-detected body portion of a healthy subject, are attenuated due to absorption by tissues in the to-be-detected body portion, and are eventually received. The attenuation of the at least three light waves is compared against the absorption spectrum of human tissues to obtain the hemoglobin level and water content of the to-be-detected body portion of the healthy subject. B. Step A is repeated on a to-be-detected body portion of a person suspected of Kawasaki disease to obtain at least three attenuated light waves and consequently the hemoglobin level and water content of the to-be-detected body portion of the person suspected of Kawasaki disease. C. A processor compares the hemoglobin level and water content of the to-be-detected body portion of the person suspected of Kawasaki disease with those of the healthy subject respectively and outputs the comparison results.

The present invention also provides a method for evaluating the treatment result of Kawasaki disease optically through the following steps:

A. At least three light waves of different wavelengths are propagated through a to-be-detected body portion of a healthy subject, are attenuated due to absorption by tissues in the to-be-detected body portion, and are eventually received. The attenuation of the at least three light waves is compared against the absorption spectrum of human tissues to obtain the hemoglobin level and water content of the to-be-detected body portion of the healthy subject. B. Step A is repeated on a to-be-detected body portion of a person with Kawasaki disease to obtain at least three attenuated light waves and consequently the hemoglobin level and water content of the to-be-detected body portion of the person with Kawasaki disease. C. A processor compares the hemoglobin level and water content of the to-be-detected body portion of the person with Kawasaki disease with those of the healthy subject respectively and outputs the comparison results.

The present invention further provides a detection device for performing the foregoing method for optical detection of Kawasaki disease, wherein the detection device includes a detection light source and a photosensor in addition to the processor.

The detection light source is configured to emit the at least three light waves of the different wavelengths. The photosensor is configured to receive the attenuated light waves. The processor is signal-connected to the detection light source and the photosensor and is configured to control the operation of the detection light source and of the photosensor and to receive and compare the hemoglobin level and water content of the to-be-detected body portion of the healthy subject and the hemoglobin level and water content of the to-be-detected body portion of the person suspected of Kawasaki disease to obtain the comparison results.

The technical features described above produce the following effects:

1. The present invention provides a non-invasive method that helps a physician clinically to diagnose or distinguish Kawasaki disease as early as possible. The method helps physicians as well as parents to make an accurate diagnosis when a child has had a fever for at least five but not more than ten days, in order for the child to receive timely treatment with high-dose immunoglobulin if necessary. Only by doing so can the risk of injury posed by Kawasaki disease to the child's heart be greatly reduced. Early and accurate diagnosis, after all, is critical to the treatment of Kawasaki disease.

2. The optical detection system of the present invention can assess the symptoms of Kawasaki disease by detecting the hemoglobin level, water content, and blood oxygen level of the tissues in a limb optically. It is therefore totally unnecessary to take blood samples from a child patient to be assessed. This entirely non-invasive detection method is a novel tool for diagnosing Kawasaki disease and features high sensitivity and specificity.

3. By developing, commercializing, and promoting the optical detection device of the present invention for carrying out the Kawasaki disease detection method disclosed herein, physicians or even parents will be enabled to diagnose and treat the tricky Kawasaki disease more efficiently and accurately, thus saving the precious lives of more children, who are the hope and driving force of our future.

4. The optical detection system of the present invention can detect the hemoglobin level, water content, and blood oxygen level of the tissues in a limb and thereby provide a basis on which to evaluate the treatment result of Kawasaki disease.

5. According to the present invention, the optically detected hemoglobin level and water content of the tissues in a limb can be further incorporated into an artificial neural network algorithm in order to provide more accurate and more clinically applicable classification of the Kawasaki disease symptoms.

DETAILED DESCRIPTION OF THE INVENTION

The foregoing technical features are incorporated into the disclosed method and device for optical detection of Kawasaki disease and of the treatment result of Kawasaki disease. The major effects of the disclosed method and device are demonstrated below by way of an embodiment.

Figure 1:
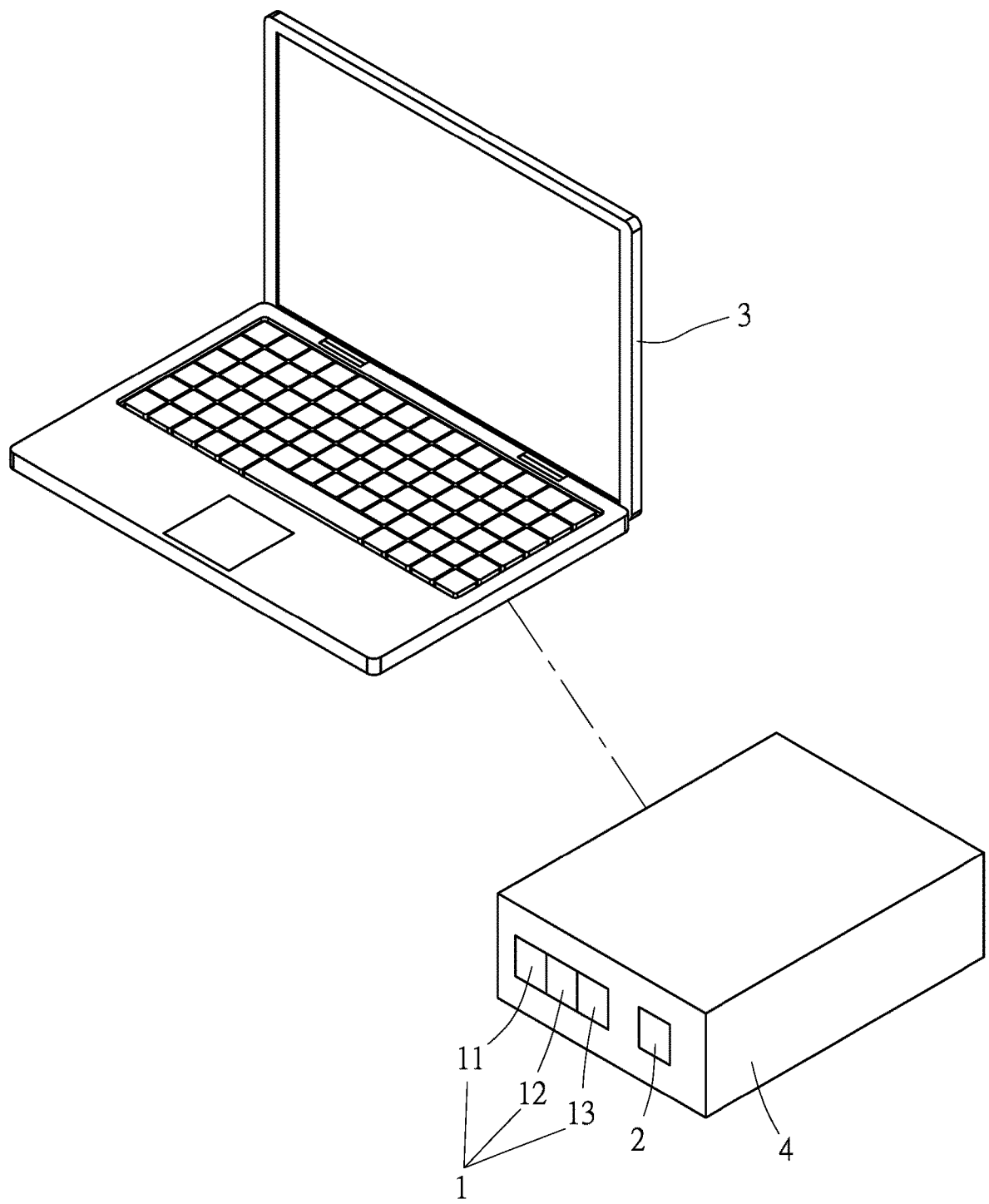
FIG. 1 schematically shows a detection device according to the present invention.

Referring to FIG. 1, a detection device according to an embodiment of the present invention includes a detection light source 1, a photosensor 2, and a processor 3.

The detection light source 1 includes a first light source 11, a second light source 12, and a third light source 13. In this embodiment, the detection light source 1 and the photosensor 2 are integrated into a control device 4. The detection light source 1 and the photosensor 2 are signal-connected to the processor 3 so that the processor 3 can control the operation of the detection light source 1 and of the photosensor 2. Preferably, the detection light source 1 and the photosensor 2 are signal-connected to the processor 3 in a wireless manner during use.

Figure 2:
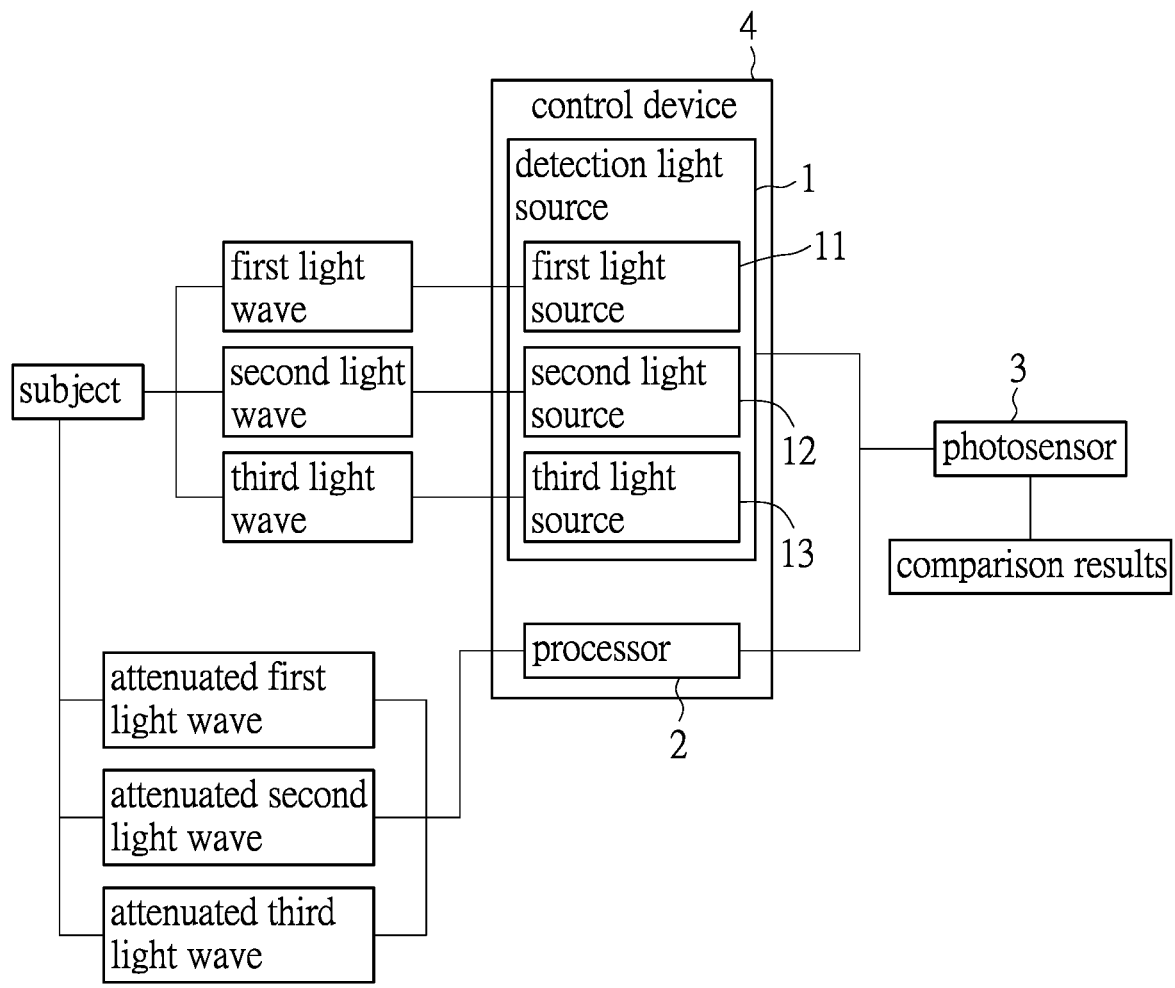
FIG. 2 is a functional block diagram showing how the detection device in FIG. 1 is used.
Figure 3:
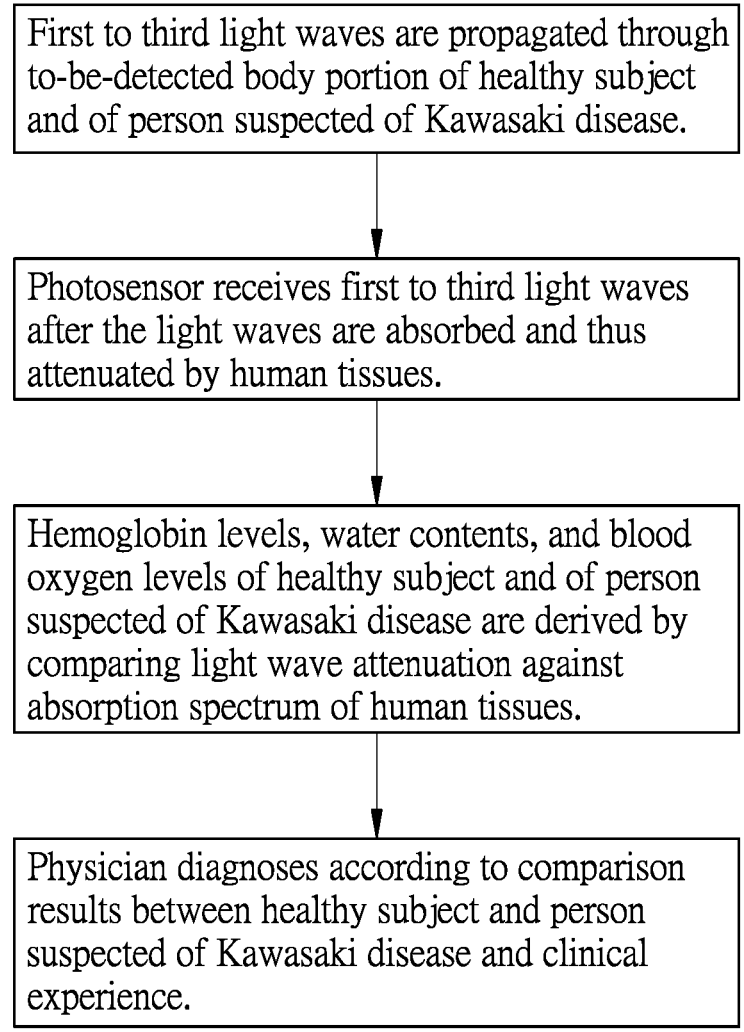
FIG. 3 is the flowchart of a detection method according to the present invention.

Referring to FIG. 2 and FIG. 3, the first light source 11 is configured for emitting a first light wave; the second light source 12, a second light wave; and the third light source 13, a third light wave. The first light wave has a wavelength ranging from 600 nm to 800 nm; the second light wave, from 800 nm to 920 nm; and the third light wave, from 920 nm to 1500 nm. In this embodiment, the wavelengths of the first to the third light waves are 700 nm, 910 nm, and 950 nm respectively. In practice, however, light waves in the visible light band and the near-infrared band are all suitable for use. The light waves in this embodiment are selected because they tend to attenuate to a relatively significant extent after passing through a target object.

Figure 4:
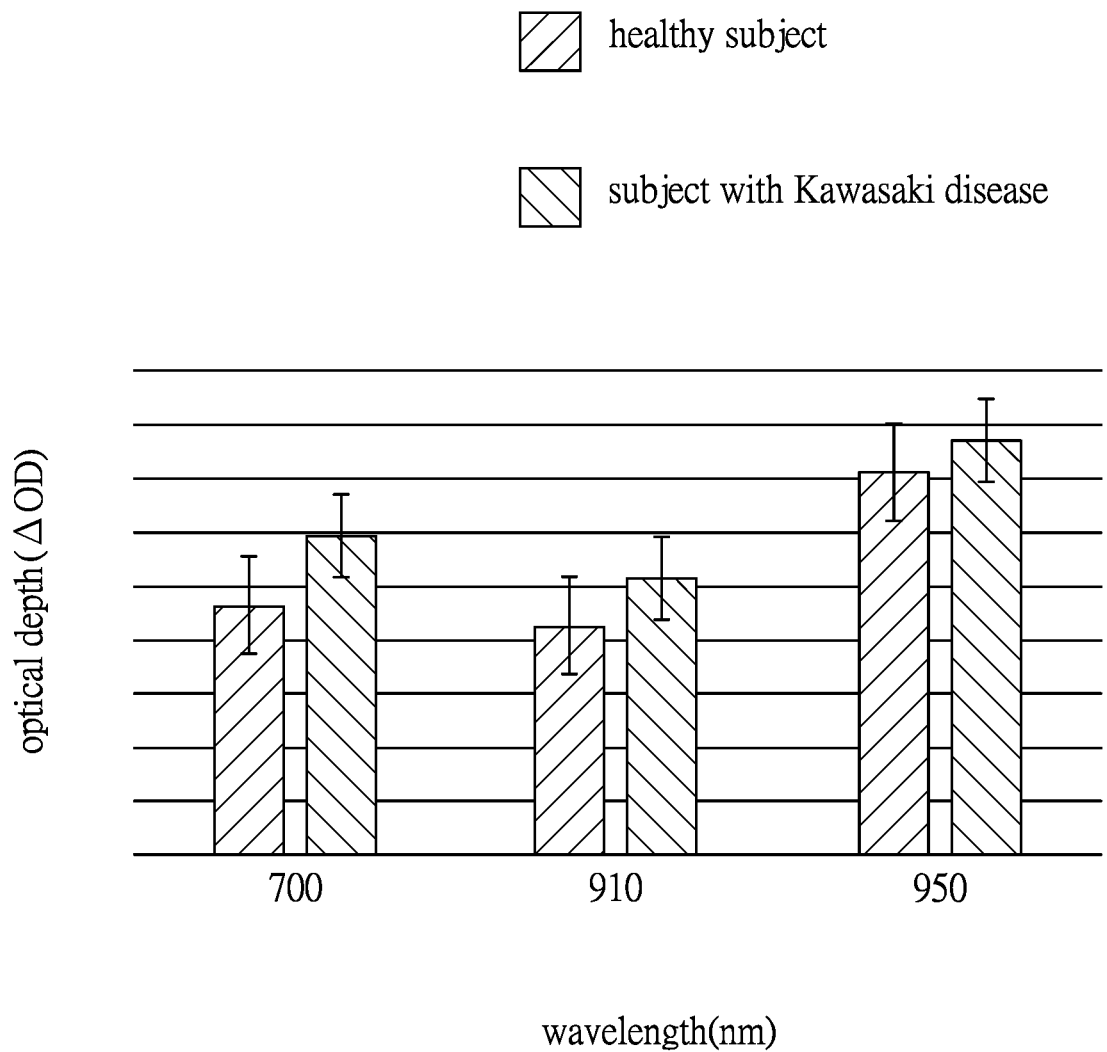
FIG. 4 shows a comparison of light attenuation, or more particularly the different degrees to which the first to the third light waves are respectively attenuated due to absorption by the tissues of a healthy subject and of a person suspected of Kawasaki disease while the present invention is carried out.
Figure 5A:
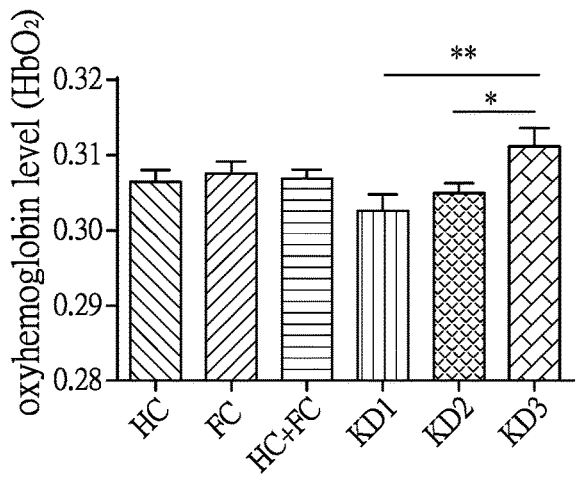
FIG. 5A shows a comparison of oxyhemoglobin levels for use in evaluating the treatment result of Kawasaki disease according to the present invention, wherein the oxyhemoglobin levels correspond respectively to an ordinary control group (healthy group), a feverish control group, a time period before treatment, a time period after treatment and before discharge from hospital, and a time period at least three weeks after treatment.
Figure 5B:
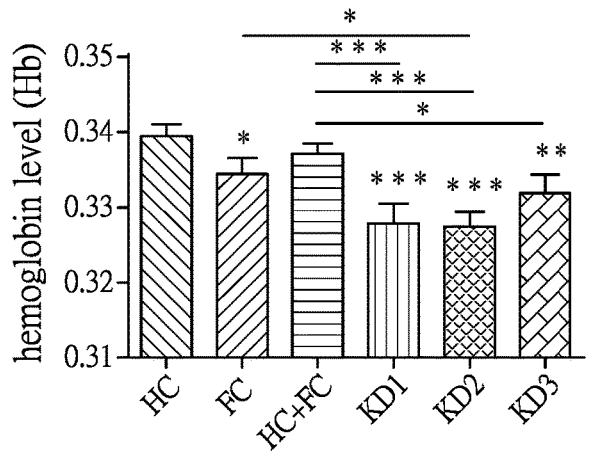
FIG. 5B shows a comparison of hemoglobin levels for use in evaluating the treatment result of Kawasaki disease according to the present invention, wherein the hemoglobin levels correspond respectively to an ordinary control group (healthy group), a feverish control group, a time period before treatment, a time period after treatment and before discharge from hospital, and a time period at least three weeks after treatment.
Figure 5C:
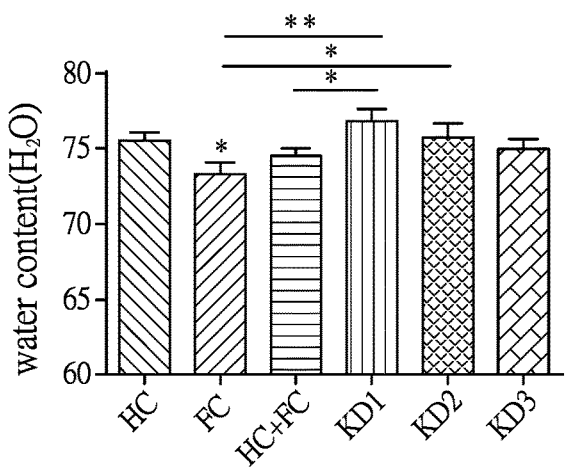
FIG. 5C shows a comparison of water contents for use in evaluating the treatment result of Kawasaki disease according to the present invention, wherein the water contents correspond respectively to an ordinary control group (healthy group), a feverish control group, a time period before treatment, a time period after treatment and before discharge from hospital, and a time period at least three weeks after treatment.
Figure 5D:
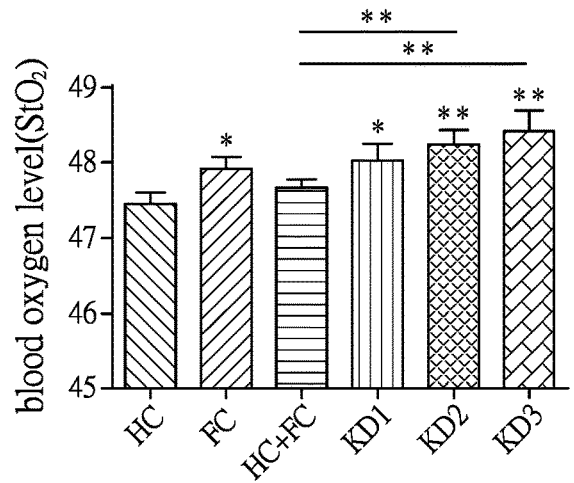
FIG. 5D shows a comparison of blood oxygen levels for use in evaluating the treatment result of Kawasaki disease according to the present invention, wherein the blood oxygen levels correspond respectively to an ordinary control group (healthy group), a feverish control group, a time period before treatment, a time period after treatment and before discharge from hospital, and a time period at least three weeks after treatment.

In this embodiment, Kawasaki disease can be detected optically by a method including the following steps:

A. The first light wave, the second light wave, and the third light wave are propagated through a to-be-detected body portion (typically one of the limbs) of a healthy subject and are received after being absorbed, and hence attenuated, by tissues in the to-be-detected body portion. The degree of light attenuation through the to-be-detected body portion of the healthy subject is then calculated, expressed by absorbance, or optical depth ($\Delta OD$), i.e., $$\Delta OD(\lambda) = -\log \frac{Io(\lambda)}{Ii(\lambda)},$$

where $I_i(\lambda)$ and $I_o(\lambda)$ represent respectively the original intensity of the incident light of wavelength $\lambda$ and the intensity of the light after it is absorbed by human tissues, as shown in FIG. 4. The hemoglobin level, water content, and blood oxygen level of the to-be-detected body portion of the healthy subject are subsequently derived from the degree of light attenuation and the absorption spectrum of human tissues.

B. The first light wave, the second light wave, and the third light wave are propagated through a to-be-detected body portion (one of the limbs, too) of a person suspected of Kawasaki disease and are attenuated as a result. The degree of light attenuation through the to-be-detected body portion of the person suspected of Kawasaki disease is calculated, as shown in FIG. 4, to obtain the hemoglobin level, water content, and blood oxygen level of the to-be-detected body portion of the person suspected of Kawasaki disease.

C. The processor 3 receives the data generated in the previous steps, compares the hemoglobin level, water content, and blood oxygen level of the to-be-detected body portion of the person suspected of Kawasaki disease with those of the healthy subject respectively, and outputs the comparison results.

It should be pointed out that the processor 3 cannot determine whether the person suspected of Kawasaki disease dose has contracted the disease solely based on the comparison results of the foregoing three parameters; a physician's clinical experience is still required for judgement. For example, in cases where the hemoglobin level is overly high but the water content and blood oxygen level are normal, or where the hemoglobin level is normal but the water content and blood oxygen level are exceedingly high, a physician must be the judge in diagnosing the person suspected of Kawasaki disease. That is to say, the values obtained from the steps described above serve only to provide physicians with informative data so that an accurate diagnosis can be made. The present invention, therefore, does not fall within the non-patentable category of "diagnostic, therapeutic, and surgical methods for the treatment of humans or animals" set forth in Paragraph 2, Article 24 of the Patent Act of Taiwan.

The present invention can be further applied to evaluate the treatment result of Kawasaki disease, as shown in FIG. 5A to FIG. 5D, which show the comparison results of oxyhemoglobin levels, hemoglobin levels, water contents, and blood oxygen levels between an ordinary control group (healthy group, HC), a feverish control group (FC), a time period before treatment (KD1), a time period after treatment and before discharge from hospital (KD2), and a time period at least three weeks after treatment (KD3). It is known that a person with Kawasaki disease tends to have a significantly lower oxyhemoglobin level and hemoglobin level but a significantly higher water content and blood oxygen level than a healthy person, so the treatment result of Kawasaki disease can be assessed by the speed at which the aforesaid parameters return to their respective normal values.

Moreover, the hemoglobin levels, water contents, and blood oxygen levels of a healthy subject and of a plurality of people with Kawasaki disease can be input into a numerical analysis model for analysis (e.g., analysis according to an artificial neural network theory or a fuzzy theory, both of which involve a non-linear model; or linear analysis by means of a linear model), in order to calculate the Kawasaki disease symptom indices of each of the people with the disease.

According to the above, the present invention provides a non-invasive optical detection method that facilitates early diagnosis of Kawasaki disease. This method is completely non-invasive because no blood samples need to be taken from child patients. As a novel tool to assist in the diagnosis of Kawasaki disease, the disclosed method can help physicians and parents make an accurate diagnosis when a child has had a fever for at least five but not more than ten days, in order for the child to receive high-dose immunoglobulin treatment if needed, and only by doing so can the risk of injury posed by Kawasaki disease to the child's heart be substantially reduced. After all, early and accurate diagnosis is key to the treatment of Kawasaki disease. The present invention can also be used to evaluate the treatment result of Kawasaki disease.

The description of the above embodiment should be able to render the operation, use, and effects of the present invention fully understandable. The embodiment, however, is only a preferred one of the invention and should not be construed as restrictive of the scope of the invention. All simple equivalent changes and modifications made according to the disclosure of this specification and the appended claims should fall within the scope of the invention.

What is claimed is:

1. A method for optical screening of a subject for Kawasaki disease, comprising:
    optically determining values for physiological parameters of a selected body portion of both a healthy subject and a subject suspected of Kawasaki disease, the physiological parameters of the selected body portion including a hemoglobin level and a water content, the optical determination for each subject including:
        propagating at least three light waves of different wavelengths through the selected body portion of the subject, the light waves being partially absorbed and thus attenuated by tissues in the selected body portion, and
        deriving the parameter values of the selected body portion of the subject based on attenuation of the light waves and on an absorption spectrum of human tissues;
    comparing the parameter values determined for the selected body portion of the subject suspected of Kawasaki disease with the parameter values determined for the selected body portion of the healthy subject respectively; and
    outputting a comparison result of the parameter values, by a processor,
    wherein the subject suspected of Kawasaki disease is non-invasively screened for Kawasaki disease based on the comparison result.

2. The method of claim 1, wherein the physiological parameters of the selected body portion further include a blood oxygen level.

3. The method of claim 2, wherein the different wavelengths of the at least three light waves range from 600 nm to 800 nm, from 800 nm to 920 nm, and from 920 nm to 1500 nm, respectively.

4. The method of claim 1, further comprising:
    inputting the parameter values of the selected body portion of the healthy subject and the parameter values of the selected body portion of a plurality of subjects with Kawasaki disease into a numerical analysis model for analysis; and
    calculating Kawasaki disease symptom indices of each of the subjects with Kawasaki disease.

5. The method of claim 4, wherein the numerical analysis model is one of a non-linear model based on an artificial neural network theory, a non-linear model based on a fuzzy theory, and a linear analysis model.

6. The method of claim 4, wherein the physiological parameters of the selected body portion further include a blood oxygen level.

7. A detection device for performing the method of claim 1 for optical screening of the subject for Kawasaki disease, comprising:
    a detection light source for emitting the light waves of the different wavelengths;
    a photosensor for receiving the attenuated light waves; and
    the processor, signal-connected to the detection light source and the photosensor and configured to:
        control operation of the detection light source and of the photosensor, derive the parameter values of the selected body portion of subjects based on the attenuation of the light waves and on the absorption spectrum of human tissues, and compare the parameter values determined for the selected body portion of the subject suspected of Kawasaki disease with the parameter values determined for the selected body portion of the healthy subject respectively to obtain the comparison result of the parameter values.

8. The detection device of claim 7, wherein the physiological parameters of the selected body portion further include a blood oxygen level.

9. The detection device of claim 7, wherein the detection light source and the photosensor are signal-connected to the processor in a wireless manner.

10. The detection device of claim 7, wherein the selected body portion is a human limb.

11. The method of claim 1, wherein the selected body portion is a human limb.

12. A method for optical evaluation of a result of a treatment of Kawasaki disease in a subject, comprising:

optically determining a hemoglobin level, a blood oxygen level, and a water content of a selected body portion of both a healthy subject and a subject with Kawasaki disease, the optical determination for each subject including:

propagating at least three light waves of different wavelengths through the selected body portion of the subject, the light waves being partially absorbed and thus attenuated by tissues in the selected body portion, and deriving the hemoglobin level, the blood oxygen level, and the water content of the selected body portion of the subject based on attenuation of the light waves and on an absorption spectrum of human tissues;

comparing the hemoglobin level, the blood oxygen level, and the water content determined for the selected body portion of the subject with Kawasaki disease with the hemoglobin level, the blood oxygen level, and the water content of the selected body portion of the healthy subject respectively; and outputting a comparison result of the hemoglobin levels, of the blood oxygen levels, and of the water contents, by a processor, wherein the result of the treatment in the subject with Kawasaki disease is non-invasively evaluated based on the comparison result.

13. The method of claim 12, wherein the selected body portion is a human limb.

\* \* \* \* \*